US007011957B2

(12) United States Patent
Lewis et al.

(10) Patent No.: US 7,011,957 B2
(45) Date of Patent: Mar. 14, 2006

(54) ISOLATION AND CULTIVATION OF MICROORGANISMS FROM NATURAL ENVIRONMENTS AND DRUG DISCOVERY BASED THEREON

(75) Inventors: Kim Lewis, Newton, MA (US); Slava S. Epstein, Dedham, MA (US); Tammi Kaeberlein, Nahant, MA (US)

(73) Assignee: Northeastern University, Boston, MA (US)

( * ) Notice: Subject to any disclaimer, the term of this patent is extended or adjusted under 35 U.S.C. 154(b) by 302 days.

(21) Appl. No.: 10/143,551

(22) Filed: May 10, 2002

(65) Prior Publication Data

US 2003/0059867 A1   Mar. 27, 2003

Related U.S. Application Data

(63) Continuation-in-part of application No. 10/135,960, filed on May 1, 2002, now abandoned, which is a continuation-in-part of application No. 60/325,052, filed on Sep. 26, 2001.

(51) Int. Cl.
*C12Q 1/04* (2006.01)
*C12Q 1/24* (2006.01)

(52) U.S. Cl. .......................... 435/34; 435/30; 435/244; 435/252.1; 435/297.1; 435/287.9; 435/288.5

(58) Field of Classification Search .................. 435/34, 435/244, 252.1, 297.1, 287.9, 288.5
See application file for complete search history.

(56) References Cited

U.S. PATENT DOCUMENTS

| | | | |
|---|---|---|---|
| 3,893,891 A | 7/1975 | Tannenbaum et al. | |
| 4,271,266 A | 6/1981 | Bergy et al. | 435/73 |
| 5,589,352 A | 12/1996 | Breznak et al. | 435/34 |
| 5,593,883 A | 1/1997 | Cano et al. | 435/252.1 |
| 5,705,378 A | 1/1998 | Yoshida et al. | 435/194 |
| 5,710,039 A | 1/1998 | Hirasawa et al. | 435/252.1 |
| 5,739,019 A | 4/1998 | Walker et al. | |
| 5,807,735 A | 9/1998 | Klibanov et al. | 435/252.33 |
| 5,837,691 A | 11/1998 | Hegde et al. | 514/29 |
| 5,849,724 A | 12/1998 | Leboul et al. | 514/75 |
| 5,897,996 A | 4/1999 | Kimbara et al. | 435/262.5 |
| 5,945,331 A | 8/1999 | Kozaki et al. | 435/262 |
| 5,972,686 A | 10/1999 | Kang et al. | 435/252.1 |
| 5,985,274 A | 11/1999 | Argoudelis et al. | 424/115 |
| 5,998,198 A | 12/1999 | Nakayama et al. | 435/262.5 |
| 6,015,706 A | 1/2000 | Kim et al. | 435/252.1 |
| 6,019,984 A | 2/2000 | MacInnes et al. | 424/255.1 |
| 6,030,779 A | 2/2000 | Short | 435/6 |
| 6,077,515 A | 6/2000 | Barbour et al. | 424/234.1 |
| 6,110,712 A | 8/2000 | Tsuchida et al. | 435/101 |
| 6,171,844 B1 | 1/2001 | Numata et al. | 435/252.1 |
| 6,323,021 B1 | 11/2001 | Wang et al. | 435/254.5 |
| 6,331,419 B1 | 12/2001 | Moriya et al. | 435/110 |

FOREIGN PATENT DOCUMENTS

| | | |
|---|---|---|
| WO | WO 97/37036 | 9/1997 |
| WO | WO 97/37036 | 10/1997 |
| WO | WO 98/14784 | 4/1998 |
| WO | WO 99/40989 | 8/1999 |
| WO | WO 01/07034 A1 | 2/2001 |

OTHER PUBLICATIONS

Jensen et al., Annu. Rev. Microbiol., vol. 48, pp. 559-584 (1994).*
Tighe et al., Indoor Air Reviews, May 1995, pp. 20-22.*
Paul R. Jensen, et al., "Strategies for the Discovery of Secondary Metabilites from Marine Bacteria: Ecological Perspectives", Annu. Rev. Microbiol., 1994, pp. 559-584.
Paul R. Jensen, et al., "Distribution of Actinomycetes in Near-Shore Tropical Marine Sediments", Applied and Environmental Microbiology, Apr. 1991, pp. 1102-1108.
William Fenical, "New Pharmaceuticals from Marine Organisms", Marine Biotechnology, TIBTECH, Sep. 1997, vol. 15, pp. 339-341.
Supreme Court of the United States, "*Diamond, Commissioner of Patens and Trademarks v. Chakrabarty*", No. 79-136, Decided Jun. 16, 1980, USPQ pp. 193-202.
Court of Customs and Patent Appeals, "In re Bergy, Coats, and Malik; In re Chakrabarty", Nos. 76-712 and 77-535, Decided Mar. 29, 1979, USPQ pp. 352-395.
"Living Organisms and the Product of Nature Doctrine", Biotechnology and the Federal Circuit, §3.2, pp. 40-41, author unknown.
Kaeberlin et al., "Isolation of "uncultivables" into Pure Culture," Abstracts of the General Meeting of the American Society for Microbiology, vol. 102, 2002, p. 468.
McFeters et al., "Survival of Coliform Bacteria in Natural Waters Field and Laboratory Studies with Membrane Filter Chambers," Applied Microbiology, vol. 24, No. 5, 1972, pp 805-811.

(Continued)

*Primary Examiner*—Irene Marx
(74) *Attorney, Agent, or Firm*—Wilmer Cutler; Pickering Hale and Dorr LLP (57) ABSTRACT

The method of the invention is directed to the novel use of a diffusion chamber within which previously "uncultivatible" microorganisms can be isolated. Rather than attempting to replicate the natural environment of an unknown microorganism, the method of the invention provides for exposing dividing microorganisms to all the components of the original environment while simultaneously containing the resulting colonies so that they can be isolated. The method of the invention can take advantage of the recognition that the preponderance of difficult-to-grow microorganisms do not form colonies visible to the naked eye. Therefore, these organisms must be isolated under a compound microscope as "microcolonies." In addition, methods according to the invention permit the isolation of novel microorganisms capable of growing in artificial media only in co-culture in the presence of a companion microorganism.

23 Claims, 3 Drawing Sheets

OTHER PUBLICATIONS

Vasconcelos et al., "Survival of Bacteria in Seawater Using a Diffusion Chamber Apparatus in Situ," Applied and Environmental Microbiology, vol. 31, No. 6, 1976, pp 913-920.

Allsopp, D., Colwell, R.R., & Hawksworth, D.L., "Microbial Diversity and Ecosystem Function" (CAB International, Wallingford, U.K., 1995) Cover page and pp 4-5 only.

Barer, M.R., & Hardwood, C.R. "Bacterial viability and culturability". Adv. Microb, Physiol. 41: 93-137 (1999).

Barns, S.M., Fundyga, R.E., Jeffries, M. W., & Pace, N.R., "Remarkable archaeal diversity detected in a Yellowstone National Park hot spring environment," *Proc. Natl. Acad. Sci.* USA 91: 1609-1613 (1994).

Bassler, B.L., "How bacteria talk to each other: regulation of gene expression by quorum sensing," *Curr. Opin. Microbiol.* 2: 582-587 (1999).

Brenner et al., Classification of Procaryotic Organisms and the Concept of Bacterial Speciation, "Bergy's Manual of Systematic Microbiology," $2^{nd}$ ed. 1 (Springer-Verlag, Berlin 2001), pp 27-31.

Butkevich, V.S., "Distribution of bacteria in the water column and sediments in the Barentsevo Sea: methodology and first results," Trans. Oceanogr. Inst. Moscow 2: 5-36 (1932).

Butkevich, V.S., "Zur Methodik der bakterioloschen Meeresutersuchungen and einige Angaben uber die Verteilung der Bakterien im Wasser und in den Buden des Barents Meeres," Trans. Oceanogr. Inst. Moscow 2: 36-39 (1932).

Cifuentes, A., Anton, J., Benlock, S., Donelly, A. Herbert, R.A. and Rodrigues-Valera, F., "Prokaryotic diversity in Zostera noltii-colonized marine sediments," *Appl. Environ. Microbiol.* 66: 1715-1719 (2000).

Clesceri, L.S., Greenberg, A.E., and Eaton, A.D., "Standard methods for the examination of water and wastewater, $20^{th}$ ed," American Public Health Association, pp 9-54-9-64, (1996).

Colwell, R.R., & Grimes, D.J., in "Nonculturable microorganisms in the environment," (eds Colwell, R.R., & Grimes, D.J.) 1-6 (ASM Press, Washington DC, pp 1-6, 2000.

DeLong, E. F., "Archaea in coastal marine environments," *Proc. Natl. Acad. Sci.* USA 89: 5685-5689 (1992).

Dojka, M.A., Harris, J.K. & Pace, N.R., "Expanding the known diversity and environmental distribution of an uncultured phylogenetic division of bacteria," *Appl. Environ. Microbiol.* 66:1617-1621 (2000).

Epstein, S.S., "Microbial food webs in marine sediments. II. Seasonal changes in trophic interactions in sandy tidal flat community," *Microb. Ecol.* 34: 199-209 (1997).

Fuhrman, J.A., McCallum, K., & Davis, A. A., "Noval major archeabacterial group from marine plankton," *Nature* 356: 148-149 (1992).

Giovannoni et al., "Evolution, Diversity and Molecular Ecology of Marine Prokaryotes," Microbial Ecology of the Oceans, pp 47-84, 2000.

Giovannoni, S.J., Britschgi. T.B., Moyer, C.L., & Field, K.G., "Genetic diversity in Sargasso Sea bacterioplankton," *Nature* 345, pp 60-63, 1990.

Grimes et al., "The Importance of Viable but Nonculturable Bacteria in Biogeochemistry," Nonculturable Microorganisms in the Environments, pp 209-227, 2000.

Jannasch, H.W., & Jones, G.E., "Bacterial populations in seawater as determined by different methods of enumeration," *Limnol. Oceanogr.* 4: 128-139 (1959).

Kaeberlein, T., Lewis, K., and Epstein, S.S., "Insolating 'Uncultivable' Microorganisms in Pure Culture in a Simulated Natural Environment," *Science*, vol. 296, pp. 1127-1129, (2002).

Lewin, R.A., "New Herpetosiphon species (Flexibacteralis)," *Can. J. Microbiol.* 16: 517-520 (1970).

Llobet-Brossa, E., Rosello-Mora, R & Amann, R.I., "Microbial community composition of Wadden Sea sediments as revealed by fluorescence in situ hybridization," *Appl. Environ. Microbiol.* 64: 2691-2696 (1998).

Lutz-Arend Mayer-Reil, L.A., "Autoradiography and epifluorescent miscrocopy combined for the determination of number and spectrum of actively metabolizing bacteria in natural waters," *Appl. Environ. Microbiol.* 36: 506-512 (1978).

Porter, K.G., & Feig, Y.S., "The use of DAPI for identifying and counting aquatic microflora," *Limnol. Oceanogr.* 25: 943-948 (1980).

Schauder et al., "The Luxs family of bacterial autoinducers: biosyntesis of a noval quorum-sensing signal molecule," *Molecular Microbiology* 41: 463-476 (2001).

Stanley, J.T., & Konopka, A., "Measurement of in situ activities of nonphotosytetic microorganisms in aquatic and terrestrial habitats," *Annu. Rev. Microbiol.* 39: 321-346 (1985).

Tenover et al., The Genera Campylobacter and Helicobacter, "Prokaryotes" pp 3488-3511, 1992.

Tiedje, J.M., "Microbial diversity: of value to whom?" ASM News 60: 524-525 (1994).

Torsvik, V., Goksoyr, J., & Daae, F.L. "High diversity in DNA of soil bacteria," *Appl. Environ. Microbiol.*, 56: 782-787 (1990).

Ward, D.M., Weller, R. & Bateson, M.M., "16s Rma sequences reveal numerous uncultured microorganisms in a natural community," *Nature* 345: 63-65 (1990).

Young, P., "Major microbial diversity initiative recommended," ASM News 63: 417-421 (1997).

ZoBell, C.E., "Marine Microbiology: a monograph on hydrobacteriology," (Chronica Botanica Co., Waltham, MA, USA, 1946).

* cited by examiner

ISOLATION AND CULTIVATION OF MICROORGANISMS FROM NATURAL ENVIRONMENTS AND DRUG DISCOVERY BASED THEREON

CROSS REFERENCE TO RELATED APPLICATIONS

This application claims the priority of U.S. provisional Application Ser. No. 60/325,052 filed Sep. 26, 2001, entitled METHOD AND DEVICE FOR CULTIVATION AND ISOLATION OF MICROORGANISMS FROM NATURAL ENVIRONMENTS, and is a continuation-in-part of U.S. Non-Provisional application Ser. No. 10/135,960 filed May 1, 2002 now abandon, entitled ISOLATION AND CULTIVATION OF MICROORGANISMS FROM NATURAL ENVIRONMENTS AND DRUG DISCOVERY BASED THEREON, the whole of which are hereby incorporated by reference herein.

STATEMENT REGARDING FEDERALLY SPONSORED RESEARCH OR DEVELOPMENT

Part of the work leading to this invention was carried out with United States Government support provided under a grant from the National Science Foundation, Grant No. OCE0102248. Therefore, the U.S. Government has certain rights in this invention.

BACKGROUND OF THE INVENTION

An estimate for the number of existing microbial species[11, 12] is $10^5$–$10^6$, but only several thousand have been isolated in pure culture[13]. Thus, the majority of microorganisms from the environment resist cultivation in the laboratory. These "uncultivables" represent 99–99.99% of all microbial species in nature[1-3]. Phylogenetic analyses of rRNA sequences, particularly 16s rRNA sequences., obtained from direct sampling of environments suggest that uncultivated organisms can be found in nearly every taxon within the Bacteria and Archaea, and several groups at the division level have been identified with no known cultivable representatives[4-10].

The principal reason for this disparity is that few microorganisms from environmental samples grow on nutrient media in Petri dishes. The discrepancy between the microbial total count and plate count is several orders of magnitude[4-10, 14-16]. Attempts to improve the recovery of microorganisms from environmental samples by manipulating growth media have been of limited success[3,15,17,18], and the phenomenon of uncultivability has become known as the "great plate count anomaly."[19] Methods of isolating and growing previously uncultivable microorganisms are clearly desirable. Such methods would transform microbiology by opening up access to the bulk of microbial diversity, thereby revolutionizing drug discovery.

BRIEF SUMMARY OF THE INVENTION

The method of the invention is directed to the novel use of a diffusion chamber as a growth chamber within which previously "uncultivatible" microorganisms can be isolated. Rather than attempting to replicate the natural environment of an unknown microorganism on a Petri dish, the method of the invention provides for exposing dividing microorganisms to all of the contents of the original environment while simultaneously providing a growth site for the microorganisms and containing the resulting colonies so that they can be isolated. Such microorganisms include but are not limited to bacteria, fungi, protozoa, viruses and microalgae. Additionally, the method of the invention preferably takes advantage of the recognition that, in some environments, the preponderance of difficult-to-grow microorganisms do not form colonies visible to the naked eye. Therefore, these organisms must be isolated under a compound microscope as "microcolonies." Finally, some of the newly isolated organisms have been discovered to be capable of growing in artificial media as a co-culture in the presence of a companion, or "helper," organism. A novel way of isolating and identifying novel organisms using such helper organisms has been developed.

Thus, in one aspect the invention is directed to a novel method for isolating and cultivating microorganisms from an environmental sample, the method including the steps of providing a sample from an environment to be tested; providing a growth chamber, which when sealed, preferably with a semi-permeable membrane, is permeable to diffusion of components from the environment but not to cells of microorganisms; mixing an inoculum from the sample with a support medium, preferably semi-solid, e.g., 0.7% agar, inside the growth chamber and sealing the chamber; incubating the sealed chamber under growth conditions in which components from the environment diffuse into the chamber and growth of microorganisms occurs; opening the chamber and examining the support medium inside the chamber for the presence of e.g., surface or indwelling colonies of microorganisms; and isolating cells from one of the colonies. The characteristics of the newly isolated cells can be compared with a database of characteristics of known microorganisms to determine novelty. For some environments, the support medium preferably is examined microscopically for the presence of microcolonies. If appropriate, multiple growth chambers may be processed simultaneously.

Some typical environments for sampling include, e.g., fresh water, seawater, sediments and soils, such as from forest, farmland, tundra, alpine region or landfill. Other useful sampling sites include specific areas in a building, e.g., a hospital, with samples being taken from a site such as the ventilation system, bathroom wall surface or hospital room surface.

In a particular aspect, the invention is directed to a method for isolating a novel microorganism from marine sediment, the method including the steps of providing a sample of marine sediment; providing a growth chamber sealable by a semi-permeable membrane that is permeable to diffusion of growth components but is not permeable to cells of microorganisms; mixing an inoculum from the sample with a semi-solid support medium, e.g. 0.7% agar, inside the growth chamber; sealing the chamber with the semi-permeable membrane while leaving an airspace between the surface of the support medium and the membrane; incubating the sealed chamber in a marine environment wherein seawater from the environment displaces the air in the airspace, thus filling the growth chamber, and growth components from the environment diffuse into the chamber and allow growth of microorganisms; removing the chamber from the marine environment, peeling off the membrane and examining the support medium microscopically for the presence of surface or indwelling microcolonies of microorganisms; isolating cells from one of the microcolonies; and comparing characteristics of the newly isolated cells with a database of characteristics of known microorganisms to determine novelty. The growth chamber according to the invention also allows for the diffusion out of waste products. Preferably, the support medium is provided as a soft, e.g., 0.7%, agar. To provide additional surface material, the soft agar may be mixed with autoclaved sand or mud.

Certain novel organisms, isolated as described above, have been found to be capable of growing on a standard rich medium in Petri dishes when in co-culture with a "helper" organism. Thus, in a separate method according to the invention, novel microorganisms are isolated that are capable of growing in artificial media only in the presence of a "helper" organism. In the first step, samples as above from the natural environment are serially diluted in an appropriate medium (e.g., sea water for marine microorganisms and fresh or rainwater for freshwater or soil microorganisms). These dilutions are mixed with cells of a "helper" species (identified as described below) such that the resulting mixtures contain approximately 10 "helper" cells/ml. The relatively low number of the "helper" cells allows for the visualization of their co-growth with any target "uncultivable" microorganisms.

The sample dilution/"helper" combinations from the previous step are then mixed with a support medium as described herein (e.g., 0.7% agar) supplemented with standard nutrients (e.g., marine broth) and poured into Petri dishes (2 to 10 ml per dish). Different Petri dishes will receive various numbers of microorganisms according to the degree of sample dilution and an invariable, low number of "helper" cells (e.g., 10–100 cells per dish). The "helper" cells will enable growth in Petri dishes of certain of the microorganisms, which growth will be detected visually as clusters of colonies surrounding a colony of a helper strain (as in FIGS. 5a–5b). Microorganisms from such a cluster of colonies are tentatively identified as being "uncultivable" when not in the presence of a "helper" organism.

Once co-growth of the potentially "uncultivable" and "helper" microorganisms has been achieved in Petri dishes, colonies of both "helper" and "new" organisms are reinoculated into separate areas of an individual Petri dish. In this way, pure cultures of each microorganism can be grown in different sectors of a single Petri dish. The potentially "uncultivable" microorganisms finally will be tested for the ability to grow alone in a Petri dish. Those that grow in the presence of a helper species but not alone in a Petri dish, even in a nutrient medium, are identified as the sought for organisms, i.e., those organisms previously thought of as "uncultivable," which are capable of growing in artificial media only in the presence of a "helper" organism.

The newly identified organism of interest, requiring a "helper" organism for growth on a Petri dish, is then tested for bioactivity. The growth of those organisms showing positive results for bioactivity can be upscaled by co-culture with a helper organism under conventional in vitro conditions on an artificial medium, and bioactive compounds can be isolated, many of which will be novel. In one aspect, the growth of an organism that grew from a diffusion chamber showing positive results for bioactivity can also be upscaled in pure culture in a number of chambers. Alternatively, in another aspect of the invention, an extract or supernatant from growing up an "uncultivable"/"helper" combination or a "helper" organism alone can be used as a source of components for growing up new organisms according to the invention. The signaling compound(s) responsible for such growth can be isolated.

Additional "helper" microorganisms from environmental samples can be identified by first isolating into pure culture populations of a number of novel "uncultivable" microorganisms. Representatives of these populations are then serially diluted in an appropriate medium (e.g., sea water in case of marine microorganisms, fresh water in case of freshwater microorganisms), combined in various ratios and mixed with a gel medium (e.g., 0.7% agar) supplemented with standard nutrients (e.g., marine broth). The various media containing individual mixtures of microorganisms are poured into Petri dishes and incubated in the laboratory. If the given mixture of cells contains representatives of synergistic partners, the latter will grow in Petri dishes. Because each Petri dish will receive a different number of microorganisms, some of them will exhibit synergistic microbial growth in the form of clusters of colonies. Each microorganism from such microbial clusters is a "helper" to other uncultivable microorganisms and will be used to grow the latter on artificial media. "Helpers" can also be identified from among "cultivable" microorganisms in a similar manner.

In another aspect of the invention, particularly appropriate for robotic implementation, a sample from an environment to be tested is inoculated directly onto a support medium, such as an agar plate, and growth of colonies of microorganisms is observed. Cells from two or more colonies are picked and screened for the ability to grow adjacent to each other on a second plate. Cells from colonies that do grow adjacent to each other are picked and screened for the ability to grow subsequently in separate plates. A novel "uncultivable" microorganism will grow adjacent to a companion but not alone.

In another aspect, the invention is directed to novel organisms isolated by the methods of the invention. Two specific microorganisms include MSC1 and MSC2, described herein.

The novel isolation methods according to the invention provide a breakthrough for the pharmaceutical industry as they allow for the isolation and cultivation of novel microorganisms with unknown metabolism, life cycle, ecology, etc. Whether or not the factors limiting and/or stimulating growth of these microorganisms are known no longer matters, even though this is a crucial consideration for traditional culturing. Novel organisms isolated by the methods of the invention are fertile sources for the isolation and identification of new lead compounds for the development of new therapeutic treatments. In addition, the invention provides a convenient way to isolate and identify clinically important organisms, some of which may be new, from, e.g., contaminated regions of a medical facility or a "sick" building.

BRIEF DESCRIPTION OF THE DRAWINGS

Other features and advantages of the invention will be apparent from the following description of the preferred embodiments thereof and from the claims, taken in conjunction with the accompanying drawings, in which:

FIG. 3 shows growth recovery of microorganisms from environmental samples in the diffusion chambers of FIG. 1a;

FIG. 5b—compound microscope).

DETAILED DESCRIPTION OF THE INVENTION

A growth chamber for carrying out the method of the invention is designed to allow for the growth, isolation into pure culture and characterization of microorganisms that are uncultivable at the present time. This desired result can be achieved because the conditions inside the chamber according to the invention closely resemble, if they are not identical to, the natural environment of the microorganisms. One version of such a chamber is formed from a solid substrate, e.g., a glass or silicon slide or stainless steel washer, having an orifice which is sandwiched by two robust membranes, e.g., polycarbonate or other inert material, glued onto the substrate. The membranes have pore sizes, e.g., 0.025–0.03 μm, that are sufficiently small to retain all microorganisms inside the chamber but which are sufficiently large to permit components from the environment to diffuse into the chamber and waste products to diffuse out of the chamber. After one membrane is sealed onto the bottom of the slide, the chamber is partially filled with a suspension of test cells in soft agar, e.g., 0.7%.

When the agar solidifies, the second membrane is used to seal the chamber, leaving an air space between the agar surface and the membrane. When such a device is incubated in the natural environment of the inoculum (e.g., seawater), the cells inside are exposed to the same components of the environment, e.g., the same nutrients, growth factors, metabolites of other species, etc., as are their counterparts growing in nature.

Initially, samples have been taken from the surface (oxygenated) layer of marine sediments (near the Marine Science Center, Northeastern University, Nahant, Mass.). Marine sediments were chosen because this environment is one of the richest on the planet in terms of microbial diversity. The oxygenated layer of the marine environment is 1) the easiest to work with; 2) fairly well studied relative to other microenvironments; 3) inhabited by aerobes, which are simpler to culture; and 4) rich in nutrients and cells ($10^9$–$10^{10}$ cells/gram, 99% uncultivable).

Marine samples have typically been collected from the surface oxygenated areas of a marine sandy tidal flat. Suspensions of cells from the samples are diluted, mixed with warm agar, or similar material that will solidify into a semi-solid support medium, and inoculated into the growth chamber. Some trials can include autoclaved sand and/or mud mixed with semi-solid agar as a solid substrate for those microorganisms that might require such specific surfaces for attachment as a condition for growth. In separate trials, various nutrients and/or electron donors (principally, proteins and polysaccharides), which might boost the growth rate of uncultivable microorganisms, can be added. For these trials, dialysis membranes with, e.g., a 10–20 kD cutoff pore size are placed under the polycarbonate membranes in order to prevent diffusion of the added polymeric nutrients out of the chamber.

For inoculation, dilutions are prepared over, e.g., three different ranges. For example, initially, dilutions can be prepared such that each chamber receives 1 to 100 "cultivable" cells (determined by plating on marine broth medium). If the number of colonies appearing in the growth chamber exceeds the number of expected cultivable cells, the growth of (previously) uncultivable microorganisms is indicated. However, it is possible that these inocula will include too many "weed" microorganisms that may overgrow other cells, including the target microbes. In this case, the dilution factor can be increased such that each device receives 1 to 100 cells as determined by total microscopy count of DAPI stained cells, or one to three orders of magnitude fewer cells than initially.

The growth chambers prepared as above are placed in the natural environment, where seawater from the environment replaces the air in the airspace. Alternatively, the natural environment may be replicated by, e.g., using a large marine temperature-controlled aquarium containing a 8–10 cm thick layer of field sediment and associated seawater. A larger number of colonies appearing in the growth chamber, exceeding the number of expected cultivable cells, will indicate the growth of (previously) uncultivable microorganisms. The growth chambers are opened by simply peeling off the top membrane, which, because of the liquid space that was left between the agar surface and the membrane, does not disturb the surface colonies. Each surface and indwelling colony is then inoculated onto a Petri dish with a rich (e.g., marine broth) nutrient medium as well as into a new growth chamber, which will be placed back into the natural environment. This procedure is carried out to look for colonies that fail to grow in a rich medium but do grow in the growth chamber. This screen will indicate which of the colonies growing in the growth chamber are potentially from microorganisms previously considered as "uncultivable."

Cells from putative "uncultivable" colonies are analyzed by 16S RNA gene sequencing. A comparison using, e.g., the online GenBank® database with known 16S RNA genes will identify the organism and will show whether or not it represents a new species/genus.

An important feature of growth chamber design is to include membranes that are not targeted as a microbial food source and that are also sufficiently robust to withstand the abrasion action of the sediment fauna and of the sediment itself. Traditional dialysis membranes can serve as a substrate for some microorganisms. Consequently, in a matter of days, devices including such membranes start losing their integrity. In addition to microbial attack, burrowing animals in marine sediments, such as nematodes, are likely to puncture these rather delicate membranes and thus allow free migration of microorganisms in and out of the chamber. The problems of integrity were solved by employing commercial polycarbonate membranes to seal the inner space of the chamber from the environment. Even sturdier membranes are available (e.g., aluminum membranes from Anopore Whatman, Inc.) should the need arise for use in even harsher environments.

The sealant used to glue the membranes to the chamber body also has specific requirements. For example, the sealant has to last for weeks while being immersed in sea water, and it also must be non-toxic for microorganisms. Super-Silicon Type 7 (Versachem Corp.), which is widely used to seal marine aquaria, was successfully used in a number of experiments. This is a very sturdy compound, which holds extremely well under most adverse conditions. In the trials reported below, the growth chambers built with this sealant did not leak for at least several weeks, after which point incubation was stopped. Tests on the sealant's toxicity proved negative as the sealant exhibited no effect on *E. coli* growth. This result corroborates well with many earlier findings.

The nature of the support medium inside the growth chamber is of primary importance to achieving microbial growth. This medium should enable microorganisms to divide and form colonies and should also allow the investigator to detect the colonies for subculturing and microbial isolation. The medium should be liquid initially at an elevated temperature, or at least sufficiently soft to mix well with an inoculum, and should solidify into a gel at the temperature of incubation. Examples of suitable media include agar, hydrogels, and silica gel. A successful basic medium is semi-solid, e.g., 0.7% agar. In its pure form (that is, with no nutrients added), agar is a poor food source and, as such, is unlikely to provide artificial enrichment for specific microbes. As a support medium, agar can be used either alone (in which case microbial growth can be expected solely based on components from the environment diffusing into the chamber from the outside) or in combination with polymers known to promote microbial growth (see below). A support medium useful in the method of the invention also includes an embodiment in which, for ease of handling, an agar/inoculum mixture is processed, e.g., to form a Gel MicroDrop (GMD) matrix (One Cell Systems, Inc., Cambridge, Mass.,) wherein, in a manner analogous to limited dilution cloning; individual GMDs have a high probability of containing 0 or 1 initial cell, and therefore 0 or 1 microcolony following incubation.

One particular problem in growing microorganisms on agar is that some microbes may require specific surfaces for attachment. In the absence of such surfaces, these organisms may be unable to divide and/or form colonies. Therefore, as indicated above, in some trials, e.g., those involving samples from marine sandy tidal flats, sterilized sand is added to the agar. This addition should satisfy the surface requirements of the majority of inoculated microorganisms from this environment.

Another potential source of uncertainty comes from the need to use warm (45° C.) agar for sample inoculation. This is dictated by the need to mix the agar and the inoculum. The increase in temperature over that from the environment of the sample may stress or even destroy some microorganisms in the inoculum. Such losses should be minimal, however, as the required temperature is within the range characteristic of natural environments. (Even in New England, over the summer time, the surface of exposed tidal flats under direct sun heats up to 40–45° C. and above.)

Many microorganisms may have gone unnoticed previously on Petri dishes because they do not form visible colonies. Prior work with marine microbes indicates that in sediments, solitary microorganisms are rare and that most microbes form microcolonies on the surface of sand grains and detrital particles. These microcolonies, which are quite small and consist only of a few dozen to several hundred cells, are many times smaller than can be detected under a dissecting microscope. It is likely that, inside the growth chamber, these microorganisms will form microcolonies no larger than they do in the field. Naturally, such colonies will be missed unless they are searched for specifically. One method of visualizing these microcolonies is under a compound microscope using vital dyes. Nomarski Differential Interference Contrast microscopy is also very useful. However, even if the cells are contrasted against the background by vital staining/Nomarski microscopy, handling these colonies for subculturing can be challenging. Therefore, appropriate ways to sample and manipulate milligrams of agar and handle very small numbers of cells have been developed. With semi-liquid agar as the growth medium, a tungsten wire has proven very useful, with or without a micromanipulator to operate it. Also of particular help is an additional prism in the microscope to compensate for the image inversion that is an almost universal feature of compound microscopes. With this modification, the microscope shows objects with no left-to-right inversion, which greatly facilitates manipulation of the tungsten wire. A microscope facility particularly suitable for handling such samples might include, e.g., a Zeiss Axioplan 2 MOT equipped for fluorescence imaging, a Nomarski/DIC microscope, a phase contrast microscope, and a state of the art imaging system (e.g., a Hamamatsu ultrafast high resolution cooled CCD camera operated by an Improvision software package OpenLab, which is capable of confocal imaging and 3-D rendering).

Finally, precautions must be taken to prevent uncontrolled growth in the growth chambers of a few versatile and quickly dividing species, conventionally called "weed" species. It is unlikely, however, that these will completely suppress the growth of the other species. After all, these "other" species do grow in the "natural" environment, a few microns away from the growth chambers. Thus, with proper care, promising, previously unculturable microbes will be detected, even in the presence of weeds.

The methods developed in the seawater environment are easily extrapolatable to other desirable environments from which samples can be taken in order to isolate previously "uncultivatable" microorganisms. For example, a terrestial sample, e.g., a soil sample taken from forest soil (e.g., from a temperate climate or a tropical rain forest), farmland, tundra, alpine soil or landfill, mixed with agar and placed in a growth chamber as described above, could be incubated in a moist soil environment taken from the original sampling site. The moisture level of the incubation environment could be increased, e.g., with the admixture of rainwater, if desired to achieve the appropriate level of diffusion of nutrients into the interior of the growth chamber. Another desirable category of sampling sites would be surface environments in medical facilities or in "sick" buildings, where not only could novel organisms be isolated but contaminating organisms, new or old, identified. In these sites, a culture of visible organisms or a swipe of an appropriately exposed surface would be placed in a growth chamber as described above. The growth chamber would then be placed in an unobtrusive site in the sampled environment so as to be exposed to airborne nutrients during the incubation period.

To obtain sufficient cell extract material for testing an isolated novel microorganism for bioactivity, a purified colony of a specific microorganism can be seeded into, e.g., 10 growth chambers, cultured in the natural environment and the resulting biomass extracted. At approximately $10^8$ cells per chamber, this amount of material is sufficient for screening for bioactivity and validation.

Further upscaling for the production of lead compounds can be carried out, e.g., by one of the following methods: (1) domestication, e.g., by selecting those that can now grow alone on artificial media, either with or without prior exposure of the culture to a mutagen; (2) cloning the genes for the biosynthetic pathway of the identified novel lead compound into a conventional host strain, such as *E. coli* or *Streptomyces coelicolor*; (3) co-culturing with a "helper" organism; or (4) propagating a colony of an uncultivable organism on artificial media from a sizeable inoculum. A "helper" organism is one that has been discovered, as described herein, as being capable of supporting the growth of certain organisms previously considered as "uncultivable" when the two are co-cultured on a standard rich medium in Petri dishes. The propagation method used to upscale the growth of an uncultivated isolate may be performed on artificial media, e.g., nutrient agar on a Petri dish, if the inoculum is made larger than a single cell. For example, a colony of an "uncultivable" organism from an environmental sample may be grown in a diffusion chamber, or cultured on an artificial medium in the presence of a "helper" organism. The colony is incubated for a period of time allowing it to reach a sufficient size. A large part of this colony is removed and placed without further dispersal onto an artificial nutrient medium in a Petri dish with incubation to achieve growth of a Adcolony on this medium. A sizable part of this new colony is then reinoculated onto a new artificial medium, repeating the inoculation step to propagate and upscale the growth of this uncultivated organism. Such propagation may produce sufficient amounts of growth-promoting substances, such as an autoinducer growth pheromone, enabling growth on artificial media.

The following examples are presented to illustrate the advantages of the present invention and to assist one of ordinary skill in making and using the same. These examples are not intended in any way otherwise to limit the scope of the disclosure.

EXAMPLE 1

Figure 1A:
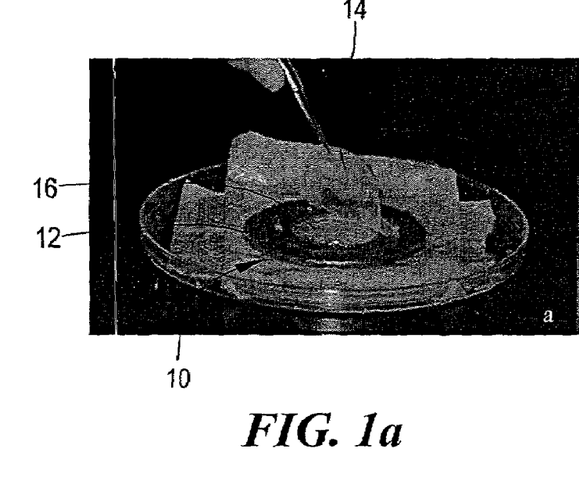
FIG. 1a shows an exemplary diffusion growth chamber for in situ cultivation of marine organisms according to the invention.

Identification of Previously Unknown Microorganisms According to the Method of the Invention Intertidal marine sediment (near the Marine Science Center, Northeastern University, Nahant, Mass., U.S.A.) was used as a source of microorganisms. The upper layer of the sandy sediment harbors a rich community of microorganisms, primarily aerobic organoheterotrophs, which reach densities of over $10^9$ cells/g[20] and are mostly uncultivated[21-22] In general, the microorganisms are separated from sediment particles by vortexing, then serially diluted and mixed with warm agar made with seawater, and, finally, placed in a diffusion chamber. Referring to FIG. 1a, an exemplary diffusion growth chamber (10) for in situ cultivation of environmental microorganisms according to the invention is formed by a stainless steel washer (12) (70 mm o.d., 33 mm i.d., 3 mm in thickness; Bruce Watkins Supply, Inc., Wilmington, N.C.) and two 0.03-$\mu$m pore-size polycarbonate membranes (14) (Osmonics, Inc., Westborough, Mass.). The membranes, glued to the washer with Silicon Glue II (General Electric, Waterford, N.Y.), enclose the inner space (16), which contains the mixture of test microorganisms and semi-solid (0.7%) agar.

Figure 1B:
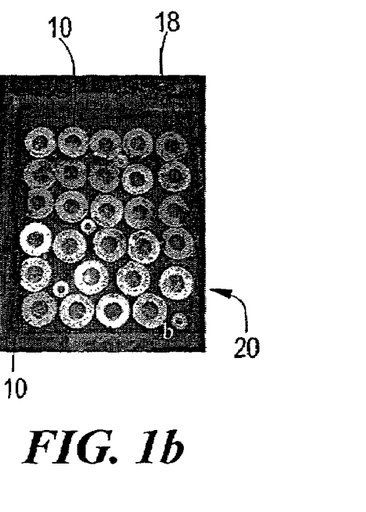
FIG. 1b shows sealed chambers according to FIG. 1a placed on the surface of marine sediment in a marine aquarium.

In practice, after the first membrane is affixed to the bottom of the washer, warm agar mixed with microorganisms from the marine sediment sample is poured in, partially filling inner space (16), and the top of the chamber is sealed with another polycarbonate membrane, leaving an air space between the top of the agar surface and the underside of the membrane. The sealed chambers (10) are placed on the surface of the sediment (18) in a marine aquarium (20), as shown in FIG. 1b, where seawater from the aquarium immediately replaces the air in the airspace. This design allows for the observation of an undisturbed agar surface when the chamber is later opened by peeling back the top membrane. Containers with these chambers are incubated in a temperature-controlled aquarium with recirculating natural seawater adjusted to 16° C.

Figure 2:
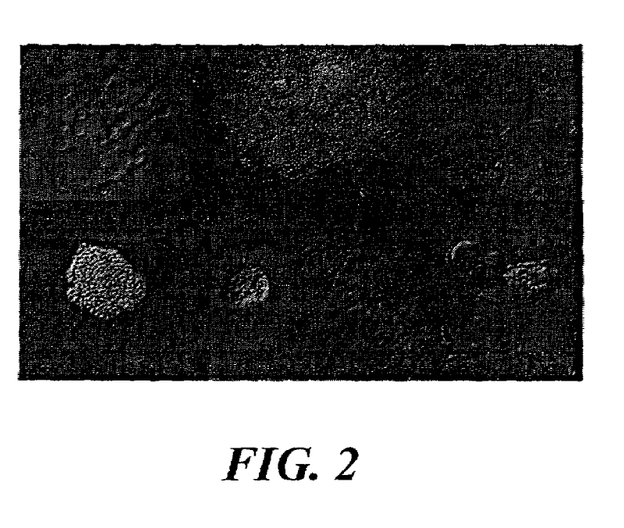
FIG. 2 shows representative colonies of marine sediment microorganisms (compound microscope view, Differential Interference Contrast (DIC)) grown in growth chambers according to the invention (scale bar, 100 $\mu$m)

In the experiments reported here, a large number of colonies of varying morphologies were observed in the chambers after one seek of incubation. FIG. 2 shows representative colonies of marine sediment microorganisms (compound microscope view, DIC—scale bar, 100 $\mu$m). Most of these (>99%) were microcolonies not visible to the naked eye. Addition of 0.01% casein increased the number of colonies in the chamber, and this supplement appeared superior to starch or marine broth tested at a variety of concentrations (0.001% to 3.7%). Therefore, 0.01% casein in 0.7% agar with seawater was used in further experiments.

Figure 3:
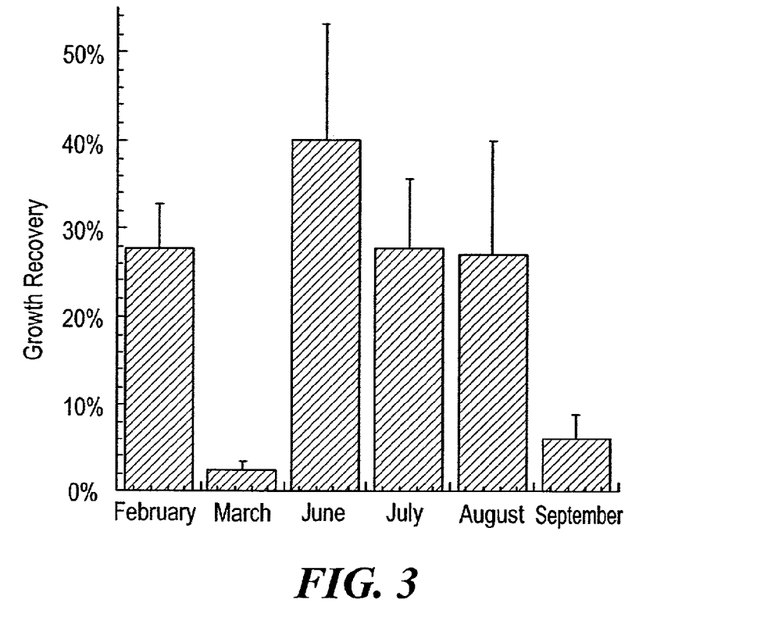

The relative effectiveness of diffusion chambers of the invention and Petri dishes with a rich medium in supporting growth of microorganisms from marine sediments was then compared. Identical samples of microorganisms from a marine sediment sample were inoculated into chambers and Petri dishes. The total number of cells in the samples was determined by direct microscopic count with DAPI staining[30]. After one week of incubation, the chambers and Petri dishes were observed for colonies. Microcolonies growing in the chambers appeared to represent a significant part of the microbial cells from the sediment. FIG. 3 shows growth recovery in diffusion chambers of microorganisms from the environmental samples. Over a period of 10 months, 13 experiments were conducted to estimate the fraction of microorganisms from marine sediment that grew in diffusion chambers. The data for the same month were averaged. Each time, approximately 20L of undisturbed tidal flat sediment was collected and placed in an aquarium with re-circulating natural seawater adjusted to 16° C. Microorganisms from the uppermost layer of these sediments were detached from sediment grains by vortexing (1 gram) for 30 seconds. Detached cells were washed out of the sediment by re-suspension in 5 ml of autoclaved seawater, followed by decantation of the supernatant. The heaviest sediment particles in the supernatant were allowed to settle, and the supernatant was subsampled (100 to 400 $\mu$l) to obtain $10^5$ to $10^6$ detached cells. The subsamples were serially diluted, mixed with warm (40° C.) agar supplemented with 0.01% technical grade casein (Sigma Aldrich, St. Louis, Mo.), and inoculated into growth chambers. After one week of incubation, microbial colonies were counted under a compound microscope equipped for DIC at 400 to 1,000×. The number of cells in the inoculum was determined by epifluorescence microscopy after staining with DAPI.

The largest rate of microbial recovery in the chambers was 40±13% of the cells inoculated and came from a sample obtained in June, 2001. There was considerable variation in the abundance of microorganisms among samplings, and the observed pattern suggests seasonality in the recovery rates. Based on the average from all samples, chambers supported growth of approximately 22±13% of the cells from the sediment. This is likely an underestimate, since the total DAPI count includes dead cells, and the fairly dormant March sample skews the recovery results.

Representative microorganisms from the chambers were successfully isolated in pure culture by transferring colonies into new chambers. Approximately 70% of all colonies produced sustainable growth in the chambers. Rather unexpectedly, a large number of microcolonies appeared on Petri dishes as well (6.3±3.5% of the number of cells inoculated). However, most of these microcolonies (86±7%) did not produce growth upon re-inoculation onto another Petri dish. It seems that the majority of microorganisms from the sediment could only undergo several divisions on a Petri dish and were incapable of sustained growth in this artificial environment. The microcolonies that did produce growth on Petri dishes upon re-inoculation (14%) appeared to represent mixed cultures. Only microorganisms that produced rapidly growing microcolonies visible to an unaided eye seemed capable of sustained growth on Petri dishes. Counting visible colonies is the conventional method of performing microbial plate count[23]. Petri dish macrocolonies made up 0.054±0.051% of the inoculum, in agreement with reports in the literature[15-17]. In the final analysis, there were about 300 times as many microorganisms producing sustainable growth in the chambers as in Petri dishes.

Figure 4A:
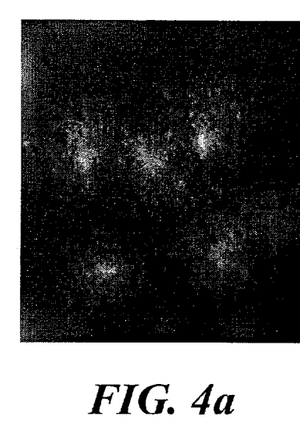
FIGS. 4a–4c show colonies and cells of MSC1 at various magnifications: (4a) Dissecting microscope view of colonies. The bar is 80 $\mu$m (4b) Compound microscope view of a single colony—DIC. The bar is 3 μm. (4c) Scanning electron microscope (SEM) view of a portion of a colony. The bar is 3 μm.
Figures 4B, 4C:
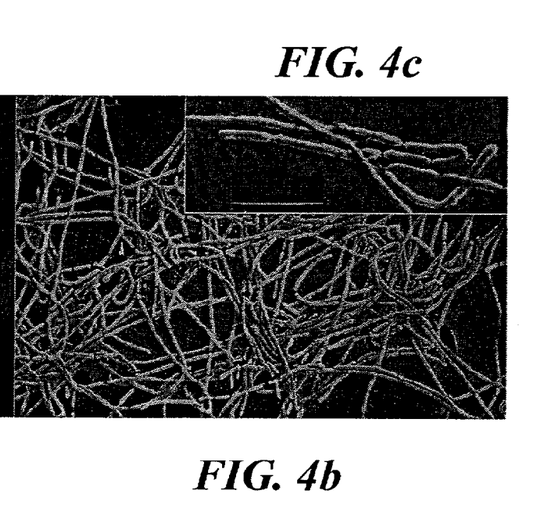

Two isolates (MSC1 and MSC2) obtained from the chambers were examined further. FIG. 4a shows a dissecting microscope view of MSC1 colonies against a dark field (scale bar length—80 μm). The bar is 80 μm in length. FIG. 4b is a compound microscope view (DIC) of a single MSC1 colony (scale bar length—3 μm). FIG. 4c is a SEM view of a portion of a colony (scale bar length—3 μm). A colony of MSC1 was isolated with the aid of a tungsten wire (75 μm shaft and <1 μm at tip; FHC, Inc., Bowdoinham, Me., U.S.A.), washed from agar in QG Buffer (Qiagen, Valencia, Calif., U.S.A.), incubated for 5 min, collected on 2.0-μm pore-size polycarbonate membranes and fixed in 2.5% EM grade glutaraldehyde. A 1400 bp sequence of 16S rDNA from MSC1 (GenBank accession #AY062176) indicates that it is a novel microorganism, with 91% sequence similarity (Jotun Hein method, the DNA Star software package) to its closest relative *Lewinella persica* (=*Herpetosiphon persicus*[24]; Class Sphingobacteria, Phylum Bacteroidetes[25]). *Lewinella persica* are filamentous bacteria with long, multicellular, unbranched cells of peach color. MSC1 differ from *Lewinella persica* and other Lewinella and Herpetosiphon in details of general colony morphology (see[24]). In general, these and other bacteria from the Cytophaga-Flexibacter-Bacterioides (CFB) group are thought to be primarily aerobic organoheterotrophs capable of extracellular digestion of complex biopolymers. Since the introduction of the 16S rRNA approach to study microbial diversity, numerous CFB sequences have been recovered from various marine environments, especially those associated with surfaces[3, 22]. The majority of the known CFB species remain uncultivated[26].

The MSC1 isolates produced colonies upon re-inoculation from chamber to chamber. It was important to examine the capability of this isolate to grow under artificial conditions. The tested strains did not generally show growth in liquid or solid artificial media (e.g., made with seawater, casein, soluble starch or marine broth). When growth of microcolonies was occasionally observed, there was no growth upon re-inoculation of these same colonies to another Petri dish. At the same time, material taken from a Petri dish did produce colonies in a chamber. It appears that cells grown in a chamber were occasionally capable of undergoing a limited number of divisions in the artificial environment of a Petri dish. This is similar to our observation of a large number of microcolonies forming on a Petri dish inoculated directly with a sediment sample. However, in the case of both the chamber to Petri dish and the environment to Petri dish inoculation, growth of the vast majority of cells was not sustainable.

EXAMPLE 2

Co-Culture Requirements of Novel Isolates

We noticed that MSC1 grew well in Petri dishes that were contaminated with certain other microorganisms. One of them (MSC2) was later isolated into pure culture in the growth chambers and identified as a novel microorganism exhibiting 95% 16S rRNA gene sequence similarity (GenBank accession # AY062177) to *Arcobacter nitrofigilis* (=*Campylobacter nitrofigilis*; Class Epsilon-proteobacteria, Phylum Proteobacteria[13]). *Arcobacter nitrofigilis* are motile, spiral curved rod-shaped bacteria, capable of nitrogen fixation and nitrate respiration, and incapable of metabolizing carbohydrates[27]. MSC2 are also curved rod-shaped bacteria and are observed to be motile. The genus *Arcobacter* is commonly found in marine sediments[21], and related 16S rRNA sequences have recently been recovered from this environment[22].

Figure 5A:
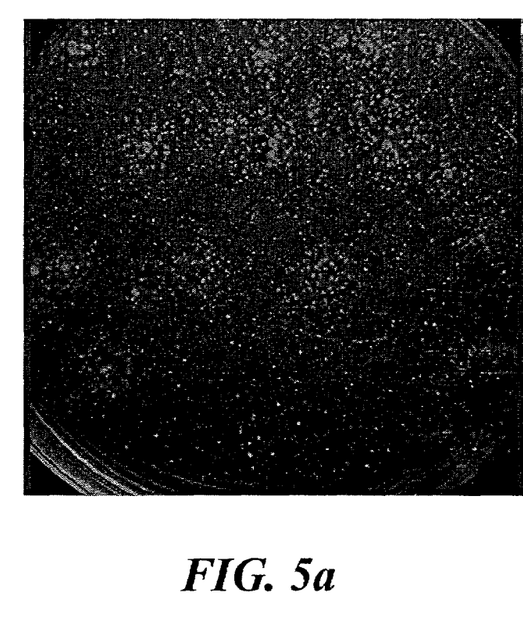
FIGS. 5a–5b show synergistic growth on Petri dishes of microorganisms isolated according to the method of the invention, MSC1 and MSC2 (FIG. 5a—dissecting microscope.
Figure 5B:
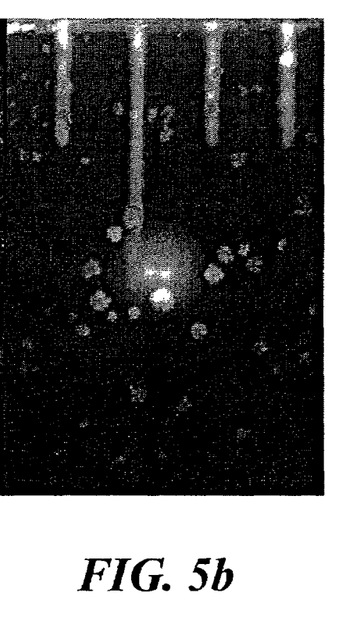

While growth of MSC1 and MSC2 could be maintained easily in separate cultures in the diffusion chamber environment, growth of these bacteria in Petri dishes was achievable only in co-culture. FIG. 5 shows synergistic growth of MSC1 and MSC2 on Petri dishes. First, colonies were collected with a tungsten wire from diffusion chambers, diluted in autoclaved seawater to approximately 100,000 (MSC1) and 10 (MSC2) cells/ml, correspondingly, mixed with warm (40° C.) agar (0.7% final concentration) supplemented with 0.01% technical grade casein, and poured into Petri dishes (35 mm diameter, 2.5 ml volume). After one week of incubation at 14° C., the dishes were examined under a dissecting microscope (dark field, 25 to 100×) and compound microscope (DIC, 400 to 1,000×). In Petri dishes, MSC1 colonies (arrows) were invariably observed surrounding a single colony of MSC2 (diamond). Scale bar, 3 mm. Denser colonies of MSC1 formed a gradient of increasing size converging on diffuse colonies of MSC2. The pattern of colonies on the Petri dishes clearly shows co-dependence of growth.

Similarly, MSC1 could be cultured in Petri dishes in co-culture with either one of the two other isolates, MSC4 and MSC5. The fact that co-occurrence transformed uncultivable microorganisms into cultivable ones on standard Petri dishes is suggestive of the nature of uncultivability for at least some environmental microbes. The observed growth synergy is unlikely to be based on trivial cross-feeding, since the medium used (technical grade casein) was rich in nutrients. It seems possible that most microorganisms may require specific signals that indicate the presence of a familiar environment, in addition to essential nutrients. For example, substances from neighboring species could serve as "growth pheromones." Both inter- and intraspecies pheromones have been described in bacteria[28,29]. This signaling hypothesis suggests that these microorganisms will not grow in an unfamiliar environment even in the presence of nutrients and explains why so many microorganisms cannot be isolated in pure culture on artificial media in vitro. Use of the diffusion chamber according to the method of the invention bypasses this limitation and allows access to a considerable part of the previously hidden biodiversity. It is possible that once isolated and grown in the presence of a signaling compound to a sufficiently large biomass, these novel microorganisms might generate a "self-pheromone" so that the need for the presence of the signaling compound may disappear when the culture is beyond a critical biomass. If this is the case, it would make the eventual cultivation of the microorganisms much easier.

Use

Beyond the intrinsic interest of discovering new microbial species, the methods of the invention have the potential to provide an important source of diverse organisms for the development and production of novel compounds, e.g., small molecules, enzymes and antibiotics, for pharmaceutical, agricultural, chemical and industrial markets. The methods described herein can be used, e.g., for the discovery of natural products with activity against diseases and conditions that afflict mammals, such as cancer, immunodeficiency virus infection, microbial infections (e.g., bacterial and fungal infections), lipid metabolism disorders, inflammation, diabetes and the like. Such natural products discovered according to the present method can serve as lead compounds in drug discovery programs. Such drug discovery programs predicated on the novel natural products obtained via the present invention can employ the logic and methods of classical medicinal chemistry, computer-aided "rational" drug design, combinatorial or parallel synthesis protocols, combinatorial or parallel assay protocols, or any possible amalgamation of these methods and approaches. Novel natural products identified by the methods of the invention, or compounds resulting from drug discovery programs based on their use as lead compounds, may be formulated and used as pharmaceutical, agricultural or veterinary agents.

The ability to detect the presence of novel natural products is central to the practice of the subject invention. In general, assays, especially high throughput assays, are carried out to detect organic molecules and the like that are produced as part of a de novo synthesis pathway. A candidate microorganism isolated as described herein is first screened for bioactivity. For example, whole cells of a specific microorganism can be screened for antimicrobial activity, e.g., by replica plating from an agar surface containing colonies of novel microorganisms according to the invention and carrying out an agar overlay screen with a test microorganism. Then, the compound responsible for the observed bioactivity can be isolated and analyzed further. In a preferred aspect, whole cells of a specific microorganism can also be screened for antimicrobial activity using the diffusion chamber as described above by, e.g., using a semi-solid medium, and where the cells grow primarily within agar and not on the surface. For example, an environmental sample containing microbial cells is diluted so that the sample contains preferably 1–100 cultivable cells. This sample is mixed with a semi-solid medium containing a test strain, e.g., *B. subtilis* at a concentration of, e.g., $10^6$ cells/ml, which is then placed in the diffusion chamber. The mixed sample is incubated to allow uncultivated cells to form colonies. The *B. subtilis* cells form uniform growth throughout the medium. Empty zones of no or little *B. subtilis* growth are present around colonies of uncultivables that produce antibiotics. These colonies are isolated and tested further. In order to improve the growth of *B. subtilis*, diffusion chambers can be withdrawn from the environment after uncultivated organisms have formed colonies. The chambers can be opened and overlaid with a layer of nutrient agar to deliver nutrients that will diffuse into the underlying layer. Growth of *B. subtilis* occurs throughout the medium, but not around the colonies of organisms producing the antibiotics. Therefore, colonies of uncultivable organisms that produce antimicrobials will inhibit growth of test strains, producing empty zones visible, for example, under a microscope.

The high throughput processing and analysis of large libraries of test extracts or compounds may be automated, e.g., using automated/robotic systems. This automation can include, for instance, such activities as: 1) arraying and storage of libraries of extracts or compounds; and 2) screening subject extracts and compounds in biological and biochemical assays. The details of the specific methods utilized will vary from one embodiment to the next, but can be readily implemented by those skilled in the art.

For example, for high throughput assays, the subject extracts or compounds may be tested for activity in high throughput biochemical or biological assays adapted for automatic readouts. For instance, extracts may be screened for antimicrobial activity by using a panel of test organisms to be read for, e.g., optical density. The method can also employ established procedures for robotic capillary electrophoresis (CE) affinity assay or multi-well plate (e.g., 96 or 384) screening. The goal is to develop an automated method that is sensitive and rapid. In addition to affinity assays, as described above, the test extracts or compounds can be tested in biochemical assays, such as competitive binding assays or enzyme activity assays. To increase throughput, it may be desirable to test pools of extracts from more than one novel organism in certain instances.

Novel bioactive compounds from organisms isolated according to the invention may be provided as pharmaceutically acceptable compositions, which comprise a therapeutically effective amount of one or more of the compounds described above, formulated together with one or more pharmaceutically acceptable carriers. Such pharmaceutical compositions may be used for testing or therapeutic purposes. The pharmaceutical compositions may be specially formulated for administration in solid or liquid form, suitable for, e.g., oral administration; parenteral administration, for example by subcutaneous, intramuscular or intravenous injection; topical application, for example, as a cream, ointment or spray applied to the skin; or intravaginally or intrarectally, for example, as a pessary, cream or foam.

The phrase "therapeutically effective compound" as used herein means that amount of a compound, material, or composition comprising a compound of the present invention which is effective for producing some desired therapeutic effect.

The phrase "pharmaceutically acceptable carrier" as used herein means a pharmaceutically acceptable material, composition or vehicle involved in carrying or transporting the subject agent from one organ or portion of the body, to another organ or portion of the body without negative effect.

Formulations of pharmaceutical compositions described herein may conveniently be presented in unit dosage form and may be prepared by conventional methods well known in the art of pharmacy. The amount of active ingredient that can be combined with a carrier material to produce a single dosage form will vary depending upon the host being treated and the particular mode of administration.

Actual dosage levels of the active ingredients in the pharmaceutical compositions described herein may be varied so as to obtain an amount of the active ingredient that is effective to achieve the desired therapeutic response for a particular patient, composition, and mode of administration, without being toxic to the patient.

The selected dosage level will depend upon a variety of factors including the activity of the particular compound (or derivative) employed, the time of administration, the rate of excretion of the particular compound being employed, the duration of the treatment, other drugs, compounds and/or materials used in combination with the particular compound employed, the age, sex, weight, condition, general health and prior medical history of the patient being treated, and like factors well known in the medical arts. A physician or veterinarian having ordinary skill in the art can readily determine and prescribe the effective amount of the pharmaceutical composition required.

Deposits

Cultures of MSC1 and MSC2 were deposited on May 9, 2002,with the American Type Culture Collection (ATCC®), 10801 University Blvd., Manassas, Va. 20110-2209, as ATCC Nos. PTA-4312 and PTA-4313, respectively.

Applicants' assignee, Northeastern University, represents that the ATCC is a depository affording permanence of the deposit and ready accessibility thereto by the public if a patent is granted. All restrictions on the availability to the public of the material so deposited will be irrevocably removed upon the granting of a patent. The material will be available during the pendency of the patent application to one determined by the Commissioner to be entitled thereto under 37 CFR 1.14 and 35 USC 122. The deposited material will be maintained with all the care necessary to keep it viable and uncontaminated for a period of at least five years after the most recent request for the furnishing of a sample of the deposited microorganism, and in any case, for a period of at least thirty (30) years after the date of deposit or for the enforceable life of the patent, whichever period is longer. Applicants' assignee acknowledges its duty to replace the deposit should the depository be unable to furnish a sample when requested due to the condition of the deposit.

While the present invention has been described in conjunction with a preferred embodiment, one of ordinary skill, after reading the foregoing specification, will be able to effect various changes, substitutions of equivalents, and other alterations to the compositions and methods set forth herein. It is therefore intended that the protection granted by Letters Patent hereon be limited only by the definitions contained in the appended claims and equivalents thereof.

REFERENCES

1. Young, P. Major microbial diversity initiative recommended. *ASM News* 63: 417–421 (1997).
2. Barer, M. R., & Harwood, C. R. Bacterial viability and culturability. *Adv. Microb. Physiol.* 41: 93–137 (1999).
3. Giovannoni, S. G., & Rappé, M. in *Microbial Ecology of the Oceans* (ed Kirchman, D. L.) 47–84 (Wiley-Liss, Inc., New York, N.Y., USA, 2000).
4. Giovannoni, S. J., Britschgi, T. B., Moyer, C. L., & Field, K. G. Genetic diversity in Sargasso Sea bacterioplankton. *Nature* 345: 60–63 (1990).
5. Torsvik, V., Goksoyr, J., & Daae, F. L High diversity in DNA of soil bacteria. *Appl. environ. Microbiol.* 56: 782–787 (1990).
6. Ward, D. M., Weller, R. & Bateson, M. M. 16S rRNA sequences reveal numerous uncultured microorganisms in a natural community. *Nature* 345: 63–65 (1990).
7. DeLong, E. F. Archaea in coastal marine environments. *Proc. natl. Acad. Sci. USA* 89: 5685–5689 (1992).
8. Fuhrman, J. A., McCallum, K., & Davis, A. A. Novel major archae-bacterial group from marine plankton. *Nature* 356: 148–149 (1992).
9. Barns, S. M., Fundyga, R. E., Jeffries, M. W., & Pace, N. R. Remarkable archaeal diversity detected in a Yellowstone National Park hot spring environment. *Proc. natl. Acad. Sci. USA* 91: 1609–1613 (1994).
10. Dojka, M. A., Harris, J. K., & Pace, N. R. Expanding the known diversity and environmental distribution of an uncultured phylogenetic division of bacteria. *Appl. environ. Microbiol.* 66: 1617–1621 (2000).
11. Tiedje, J. M. Microbial diversity: of value to whom? *ASM News* 60: 524–525 (1994).
12. Allsopp, D., Colwell, R. R., & Hawksworth, D. L. *Microbial Diversity and Ecosystem Function* (CAB International, Wallingford, U.K, 1995).
13. Staley, J. T., Bryant, M. P., Pfennig, N., & Holt, J. G. (eds) *Bergey's Manual of Systematic Bacteriology* (Williams & Wilkins, Baltimore, Md., USA, 1989).
14. Butkevich, V. S. Zür Methodik der bakterioloschen Meeresuntersuchungen und einige Angaben über die Verteilung der Bakterien im Wasser und in den Büden des Barents Meeres. *Trans. Oceanogr. Inst. Moscow* 2: 5–39 (1932).
15. Jannasch, H. W., & Jones, G. E. Bacterial populations in seawater as determined by different methods of enumeration. *Limnol. Oceanogr.* 4: 128–139 (1959).
16. ZoBell, C. E. *Marine Microbiology: a monograph on hydrobacteriology* (Chronica Botanica Co., Waltham, Mass., USA, 1946)
17. Meyer-Reil, L. A. Autoradiography and epifluorescent microscopy combined for the determination of number and spectrum of actively metabolizing bacteria in natural waters. *Appl. environ. Microbiol.* 36: 506–512 (1978).
18. Colwell, R. R., & Grimes, D. J. in *Nonculturable microorganisms in the environment* (eds Colwell, R. R., & Grimes, D. J) 1–6 (ASM Press, Washington D.C., USA, 2000).
19. Staley, J. T., & Konopka, A. Measurement of in situ activities of nonphotosynthetic microorganisms in aquatic and terrestrial habitats. *Annu. Rev. Microbiol.* 39: 321–346 (1985).
20. Epstein, S. S. Microbial food webs in marine sediments. II. Seasonal changes in trophic interactions in a sandy tidal flat community. *Microb. Ecol.* 34: 199–209 (1997).
21. Llobet-Brossa, E., Roselló-Mora, R., & Amann, R. I. Microbial community composition of Wadden Sea sediments as revealed by fluorescence in situ hybridization. *Appl. environ. Microbiol.* 64: 2691–2696 (1998).
22. Cifuentes, A., Anton, J., Benllock, S., Donelly, A. Herbert, R. A. and Rodrigues-Valera, F. Prokaryotic diversity in *Zostera noltii*-colonized marine sediments. *Appl. environ. Microbiol.* 66: 1715–1719 (2000).
23. Clesceri, L. S., Greenberg, A. E., and Eaton, A. D. *Standard methods for the examination of water and wastewater*, 20$^{th}$ ed. American Public Health Association. Washington, D.C. (1998).
24. Lewin, R. A. New Herpetosiphon species (Flexibacteralis). *Can. J. Microbiol.* 16: 517–520 (1970).
25. Boone, D. R., Castenholz, R. W., & Garrity, G. (eds) *Bergey's Manual of Systematic Bacteriology*, 2$^{nd}$ ed. 1 (Springer-Verlag, Berlin, 2001)
26. Grimes, D. J., Mills, A. L., & Nealson, K. H. in *Nonculturable microorganisms in the environment* (eds Colwell, R. R., & Grimes, D. J) 209–227 (ASM Press, Washington D.C., USA, 2000).
27. Tenover, F. C., & Fennel, C. L. in *Prokaryotes* (eds Ballows, A., Trüper, H. G., Dworkin, M., Harder, W., & Schleifer, K.-H.) 3488–3511 (Springer-Verlag, Berlin, 1992)
28. Bassler, B. L. How bacteria talk to each other: regulation of gene expression by quorum sensing. *Curr. Opin. Microbiol.* 2: 582–587 (1999).
29. Schauder, S., Shokat, K., Surette, M. G., & Bassler, B. L. The LuxS family of bacterial autoinducers: biosynthesis of a novel quorum-sensing signal molecule. *Molecular Microbiology* 41: 463–476 (2001).
30. Porter, K. G., & Feig, Y. S. The use of DAPI for identifying and counting aquatic microflora. *Limnol. Oceanogr.* 25: 943–948 (1980).

What is claimed is:

1. A method for isolating a microorganism from an environmental sample, the method comprising the steps of:
   a) providing a sample from a natural environment to be tested;
   b) providing a growth chamber, the growth chamber when sealed with a semi-permeable membrane being permeable to components from the natural environment from which the sample was provided, but not permeable to cells of the microorganism;
   c) mixing the sample with a semi-solid support medium;
   d) placing the mixture from step c) inside the growth chamber;
   e) sealing the chamber;
   f) incubating the sealed chamber in the natural environment from which the sample was provided, under growth conditions such that components from the environment diffuse into the chamber and growth of the microorganism occurs;
   g) examining the support medium for the presence of colonies of the microorganism; and
   h) isolating cells from one of the colonies.

2. The method of claim 1, wherein the environment to be tested is selected from the group consisting of fresh water, seawater, sediments, and soils.

3. The method of claim 2, wherein the soils comprise forest soil, farmland, tundra, alpine soil, or landfill.

4. The method of claim 1, wherein, in the mixing step, the support medium is soft agar.

5. The method of claim 4, wherein the soft agar is 0.7% agar.

6. The method of claim 1, wherein the semi-permeable membrane has a pore size of 0.025 $\mu$m to 0.03 $\mu$m.

7. The method of claim 4, wherein, in the mixing step, said inoculum and the soft agar are further mixed with autoclaved sand or mud.

8. The method of claim 1, wherein, in the examining step, said surface is examined microscopically for the presence of microcolonies of microorganisms, and wherein, further, in the isolating step, cells are isolated from one of the microcolonies.

9. The method of claim 1, further comprising identifying the isolated microorganism.

10. The method of claim 1, wherein the growth chamber is sealed with a polycarbonate membrane.

11. The method of claim 1, wherein, in the mixing step, the support medium is selected from the group consisting of agar, hydrogels, and silica gel.

12. A method for isolating a microorganism from an environmental sample, the method comprising the steps of:
   a) providing a sample from a natural environment to be tested;
   b) providing a growth chamber, the growth chamber when sealed with a semi-permeable membrane being permeable to components from the natural environment from which the sample was provided, but not permeable to cells of microorganisms;
   c) mixing the sample with a support medium;
   d) processing the inoculum and the support medium to form a gel microdrop matrix;
   e) depositing the gel microdrop matrix comprising the sample in the growth chamber;
   f) sealing the chamber;
   g) incubating the sealed chamber in the natural environment from which the sample was provided, under growth conditions such that components from the environment diffuse into the chamber and growth of the microorganism occurs;
   h) examining the support medium in the gel microdrops for the presence of colonies of the microorganisms; and
   i) isolating cells from one of the colonies.

13. The method of claim 12, further comprising identifying the isolated microorganism.

14. The method of claim 12, wherein the semi-permeable membrane has a pore size of 0.025 $\mu$m to 0.03 $\mu$m.

15. The method of claim 12, wherein the growth chamber is sealed with a polycarbonate membrane.

16. A method for isolating a microorganism from a marine sediment, the method comprising the steps of:
   a) providing a sample of the marine sediment;
   b) providing a growth chamber, the growth chamber when sealed with a semi-permeable membrane being permeable to growth components of a marine environment from which the sample was provided, but not permeable to cells of microorganisms;
   c) mixing the sample with a semi-solid support medium;
   d) placing the mixture from step c) inside the growth chamber;
   e) sealing the chamber with the semi-permeable membrane;
   f) incubating the sealed chamber in the marine environment from which the sample was provided, wherein components from the marine environment diffuse into the chamber and growth of the microorganism occurs;
   g) examining the support medium microscopically for the presence of microcolonies of the microorganism; and
   h) isolating cells from one of the microcolonies.

17. The method of claim 16, wherein, in the mixing step, the support medium is soft agar.

18. The method of claim 17, wherein, in the mixing step, the inoculum and the soft agar are further mixed with autoclaved sand or mud.

19. The method of claim 17, wherein said soft agar is 0.7% agar.

20. The method of claim 16, further comprising identifying the isolated microorganism.

21. The method of claim 16, wherein, in the mixing step, the support medium is selected from the group consisting of agar, hydrogels, and silica gel.

22. The method of claim 16, wherein the semi-permeable membrane has a pore size of 0.025 $\mu$m to 0.03 $\mu$m.

23. The method of claim 16, wherein the growth chamber is sealed with a polycarbonate membrane.

* * * * *